United States Patent [19]

Zeuthen et al.

[11] Patent Number: 5,206,144
[45] Date of Patent: Apr. 27, 1993

[54] DETERMINATION OF GLYCATED (GLYCOSYLATED) HEMOGLOBIN IN BLOOD

[75] Inventors: Jesper Zeuthen, Virum; Annette Prento, Ballerup; Viggo Kruse, Skovlunde, all of Denmark

[73] Assignee: Novo Industri A/S, Denmark

[21] Appl. No.: 607,766

[22] Filed: Oct. 30, 1990

Related U.S. Application Data

[63] Continuation of Ser. No. 248,250, Sep. 19, 1988, abandoned, which is a continuation of Ser. No. 844,854, Mar. 27, 1986, abandoned.

[30] Foreign Application Priority Data

Mar. 29, 1985 [DK] Denmark ............................ 1453/85

[51] Int. Cl.$^5$ .................. G01N 33/543; G01N 33/577
[52] U.S. Cl. .................... 435/7.25; 435/7.5; 435/7.92; 436/501; 436/518; 436/531; 436/548
[58] Field of Search ............ 435/7.5, 7.92, 172.2, 435/240.27, 948, 7.25; 436/501, 518, 531, 548, 809; 935/110

[56] References Cited

U.S. PATENT DOCUMENTS

| | | | |
|---|---|---|---|
| 4,187,075 | 2/1980 | Noller | 436/531 |
| 4,228,237 | 10/1980 | Hevely et al. | 435/7 |
| 4,247,533 | 1/1981 | Cerami et al. | 424/1 |
| 4,478,744 | 10/1984 | Mezei et al. | 424/85 |
| 4,497,900 | 2/1985 | Abram et al. | 436/518 |
| 4,629,692 | 12/1986 | Dean | 436/518 |
| 4,658,022 | 4/1987 | Knowles et al. | 436/548 |
| 4,727,036 | 2/1988 | Knowles et al. | 435/240.27 |
| 4,778,752 | 10/1988 | Curtiss et al. | 435/7 |
| 4,797,473 | 1/1989 | Tarsio et al. | 435/7 |
| 4,806,468 | 2/1989 | Wagner et al. | 435/7 |
| 4,876,188 | 10/1989 | Smith et al. | 435/7 |

FOREIGN PATENT DOCUMENTS

| | | |
|---|---|---|
| 124366 | 11/1984 | European Pat. Off. |
| 185870 | 7/1985 | European Pat. Off. |
| 1580318 | 12/1980 | United Kingdom |

OTHER PUBLICATIONS

*Biotechnology* (catalogue of Fisher Scientific Co. 1983) p. 97.
Cooper Biomedical Research Products Catalogue, Mar. 1, 1985, pp. 15–16.
M. Roth, *Clin. Chem.*, 29, 1991 (1983).
J. S. Schwartz et al., *Annals of Intern. Med.*, 101, 710–713 (1984).
R. E. Dickerson and I. Geis, *Hemoglobin: Structure, Function, Evolution, and Pathology*, pp. 40–41, The Benjamin/Cummings Publ. Co. (1983).
*Clinical Chemistry*, vol. 27, No. 11, Nov. 1981, pp. 1797–1806, Easton, Penna., US; E. D. Sevier et al.: "Monoclonal antibodies in clinical immunology" *Whole article*.

*Primary Examiner*—David Saunders
*Attorney, Agent, or Firm*—Sterne, Kessler, Goldstein & Fox

[57] ABSTRACT

The concentration of glycated hemoglobin, HbA$_{1c}$, in hemoglobin from diabetic patients is regarded as a useful means of assessing the adequacy of diabetes control. This invention comprises a monoclonal antibody which, due to its specific binding of HbA$_{1c}$, can be used for the determination of HbA$_{1c}$ in the absence of prior denaturation, in blood samples by such analytical methods as radioimmuno assay or enzyme-linked immunosorbent assay. The invention also comprises hybridoma cell lines which produce monoclonal antibodies of the invention.

13 Claims, 4 Drawing Sheets

DETERMINATION OF GLYCATED (GLYCOSYLATED) HEMOGLOBIN IN BLOOD

REFERENCE TO RELATED APPLICATIONS

This application is a continuation of application Ser. No. 07/248,250, filed on Ser. 19, 1988 and now abandoned, which is a continuation of application Ser. No. 06/844,854, filed on Mar. 27, 1986 and now abandoned.

The present invention relates to monoclonal antibodies generated against glycated (glycosylated) hemoglobin and to the use of such monoclonal antibodies for monitoring the extent of glycation (glycosylation) of hemoglobin.

BACKGROUND OF THE INVENTION

Glycated (glycosylated) hemoglobins have gained acceptance as a relevant index of long-term blood glucose control in patients with diabetes mellitus. As used subsequently in this specification the term glycated hemoglobin refers to relatively stable condensation products of hemoglobin with glucose (and possibly glucose phosphates), as compared with more labile hemoglobin-glucose adducts, supposedly of the aldimine (Schiff base) type and generated by a non-enzymatic reaction between glucose and amino groups of hemoglobin. The latter are believed to be converted into the stable (formerly termed "glycosylated") type an Amadori rearrangement (cf. M. Roth: Clin.Chem. 29 (1983) 1991).

Glycated hemoglobin A components were first recognized when hemoglobin A was subjected to electrophoresis and cation exchange chromatography. Owing to their more negative charge and consequently higher electrophoretic migration rates towards the anode than that of the major component hemoglobin A (HbA$_o$) they were named the "fast" hemoglobins (HbA$_1$). The fast hemoglobins constitute a series of minor hemoglobins among which inter alia HbA$_{1a}$, HbA$_{1b}$ and HbA$_{1c}$ have been identified according to their differential migration rates. Of these HbA$_{1c}$ is present in greatest quantity in erythrocytes both from normal subjects and from diabetic patients. HbA$_{1c}$ is known to be glycated at the N-terminal. valine of the $\beta$-chains of hemoglobin A. However, recent studies have indicated that glycation may also occur at the amino group of lysine side chains and that all hemoglobins, including HbA$_o$ and HbA$_{1c}$, may comprise such glycated sites. The labile (aldimine) precursor of HbA$_{1c}$ (usually referred to as "pre-HbA$_{1c}$") is not encompassed by the above definition of HbA$_{1c}$.

It is now generally accepted that the level of HbA$_{1c}$ in a blood sample is a good index for the individual's glycemic control. Normal adults have about 90% of their total hemoglobin A as HbA$_o$ and 3–6% as HbA$_{1c}$, the balance consisting of other minor hemoglobins including HbA$_{1a}$ and HbA$_{1b}$. However, the level of HbA$_{1c}$ in patients with type 1 (juvenile) and type 2 (maturity-onset) diabetes ranges from about 6% to about 15%. The quantification of the HbA$_{1c}$ level in diabetic patients is regarded as a useful means of assessing the adequacy of diabetes control, in that such measurements represent time-averaged values for blood glucose over the preceding 2–4 months (cf. J. S. Schwartz et al.: Annals of Intern. Med. 101 (1984) 710–713).

The ideal laboratory method for measuring HbA$_{1c}$ should be specific (e.g. not influenced by the presence of pre-HbA$_{1c}$) accurate, precise, easily standardized, inexpensive and facile. Unfortunately, the methods currently available such as cation exchange chromatography, high performance liquid chromatography (HPLC), affinity chromatography or electrophoresis (isoelectric focusing) do not meet all of these criteria simultaneously. For a general review of these methods and their attempted implementation for diabetes control, reference is made to J. S. Schwartz et al., supra.

The direct measurement of glycated hemoglobin based on immunological methods has been suggested in the prior art. In this respect reference is made inter alia to British Patent No. 1.580.318 and to U.S. Pat. No. 4.478.744. The method devised in the former requires comparatively large amounts of human HbA$_{1c}$ for immunization and the latter makes use of a laboriously synthesized peptide for preparation of the antigen. In both instances the immunoassay is conducted with animal antiserum or fractions thereof containing so-called polyclonal antibodies. Such polyclonal antibodies are difficult to prepare in a reproducible manner and are generally not regarded as sufficiently specific for the assay of HbA$_{1c}$ in a highly complex mixture of closely related hemoglobin molecules.

It is the object of the present invention to overcome the drawbacks of the methods known heretofore for laboratory measurements of the extent of glycation, of hemoglobin A. The invention is based on the surprising observation that it is possible by using appropriate immunization, screening and selection procedures to isolate cell lines (hybridomas) which produce monoclonal antibodies that will bind specifically to epitopes containing glycated amino groups of hemoglobin, such as that of the N-terminal valine of the $\beta$-chains of hemoglobin A, whereas substantially less or essentially no binding occurs to the corresponding non-glycated site.

In particular, the generation of antibodies recognizing the glycated N-terminal valine residues of the HbA$_{1c}$ $\beta$-chains is a surprising achievement in view of the fact that models of the hemoglobin molecule based on X-ray crystallographic studies indicate that these residues, at least in their non-glycated state, are buried in a central cavity of the molecule and hence would be expected to be difficultly accessible to such large molecules as immunoglobulin antibodies. This cavity encompasses the so-called 2,3-diphosphoglycerate (DPG)-pocket wherein the much smaller DPG molecule is trapped between the N-terminal ends of the two, $\beta$-chains of deoxyhemoglobin. When the $\beta$-chains come closer together in oxyhemoglobin, the DPG molecule is pushed out of its binding pocket. For illustration, see R. E. Dickerson and I. Geis in "Hemoglobin: Structure, Function, Evolution, and Pathology" p. 40 (The Benjamin/Cummings Publ. Co., 1983).

SUMMARY OF THE INVENTION

The present invention provides a monoclonal antibody characterized by being of rodent, preferably of murine, origin and, furthermore, by its binding in an essentially specific manner to an epitope of human hemoglobin, which epitope comprises the glycated amino group of the N-terminal valine residue of the hemoglobin A $\beta$-chain.

The invention also provides a monoclonal antibody of rodent, preferably of murine, origin exhibiting a preferential binding to HbA$_{1c}$ as compared with its binding to HbA$_o$. According to a preferred embodiment of the invention the monoclonal antibody is in a detectably labelled, e.g. biotinylated, form.

According to a further aspect of the present invention there is provided a method for preparing a monoclonal antibody for use as a diagnostic aid for the determination of glycated human hemoglobin. The process comprises the cultivation in a suitable growth medium of a hybridoma cell line capable of producing an antibody which binds in a preferential manner an epitope comprising the glycated amino group of the N-terminal valine residue of the hemoglobin β-chain. The process for preparing such an antibody may comprise the following steps:

(a) immunizing a rodent, preferably mouse, with $HbA_{1c}$, (b) immortalizing the antibody-producing cells by fusing them with myeloma cells to produce hybridoma cells, (c) selecting by differential screening such hybridoma cells which produce an antibody showing a preferential binding to $HbA_{1c}$ as compared with its binding to $HbA_o$, and (d) culturing such selected hybridoma cells either in vitro in a suitable tissue culture medium, or in vivo in a histocompatible body fluid, followed by separation of said medium from hybridoma cells and optionally, purification of the monoclonal antibody generated therein.

Accordingly to still another aspect the present invention provides a hybridoma cell line capable of producing a monoclonal antibody showing a preferential binding to $HbA_{1c}$. Preferred hybridoma cell lines of the invention are cell lines designated HEM 13F1 and HEM 13F2, and reclones thereof.

Furthermore, there is provided a diagnostic method for the determination of $HbA_{1c}$ in a human hemoglobin source which comprises contacting the hemoglobin with a monoclonal antibody of the invention, preferably in a detectably labelled form. There is also provided a kit for the determination of $HbA_{1c}$ in a human hemoglobin source, which kit comprises a monoclonal antibody of the invention. More particularly, there is provided a kit comprising a carrier means being compartmentalized to receive in close confinement therein two or more containers—a first container containing a monoclonal antibody of the invention, preferably in a detectably labelled form—and a second container containing hemoglobin with predetermined concentration of $HbA_{1c}$. The kit preferably further comprises a third container containing hemoglobin with a predetermined concentration of $HbA_{1c}$, said predetermined concentration of $HbA_{1c}$ of said third container being different from said predetermined concentration of $HbA_{1c}$ of said second container.

DETAILED DESCRIPTION OF THE INVENTION

Figure 1:
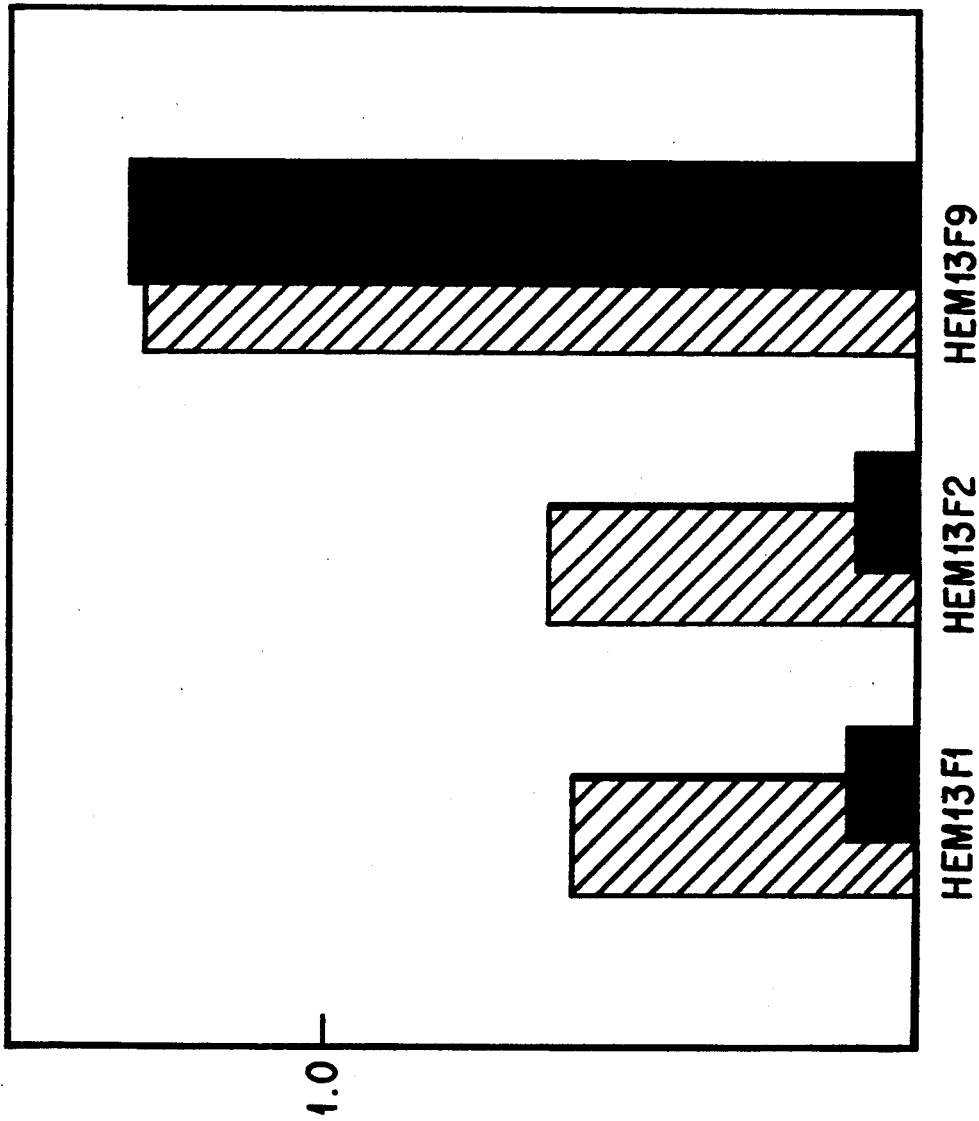
FIG. 1 illustrates results from the primary screening of hybridoma supernatants from a total of ten microtiter plates, each with 96 wells for binding to purified $HbA_{1c}$ and essentially non-glycated $HbA_o$ (as hereinafter defined). The hybridomas were obtained by fusion of spleen cells from two RBF/Dn mice with FOX-NY myeloma cells. The binding of antibody from the hybridomas HEM 13F1 and HEM 13F2 as well as that from an unspecific hybridoma, HEM 13F9, to $HbA_{1c}$ (hatched bars) and $HbA_o$ (solid bars), respectively, is shown.

The selection of monoclonal antibodies having a sufficiently preferential specificity for the purpose of this invention is facilitated by the accessability both of the selected glycated human hemoglobin essentially freed of its non-glycated counter-part, as well as of the latter containing essentially no glycated contaminants. Human $HbA_{1c}$, glycated at the N-terminal valine of the β-chains and possibly containing additional glycated lysine residues, was purified by conventional procedures such as cation exchange chromatography or HPLC. Purified $HbA_o$ (i.e. hemoglobin A essentially without glycated N-terminal valine residues) can also be obtained by such methods. If desired, contamination of $HbA_o$ with components containing glycated lysine residues can be reduced to a minimum, for example by subjecting a hemolysate of erythrocytes to anion exchange chromatography in the presence of borate as described by R. Shapiro et al. (J.Biol.Chem. 255 (1980) 3120–3127) Hereinafter such purified $HbA_o$ is referred to as essentially non-glycated $HbA_o$.

Antibodies against $HbA_{1c}$ were raised in rodents, for example in mice, wherefrom antibody-producing cells, such as spleen cells, were immortalized by fusion with suitable myeloma cells to produce hybridoma cells. Supernatants from cultures of the hybridoma cells, usually cultivated for several days, were screened for antibodies exhibiting positive binding to the immunizing antigen ($HbA_{1c}$) and essentially no binding to non-glycated $HbA_o$ for example by using an enzyme-linked immunosorbent assay (ELISA).

Primary Screening Procedure

Microtiter plates were coated by adsorption with $HbA_{1c}$ prepared by chromatography on Bio-Rex ® 70 (H. F. Bunn et al.: J.Clin.Invest. 57 (1976) 1652–1659) or with essentially non-glycated $HbA_o$. The ELISA used was a modification of the precedure described by A. Voller and E. de Savigny (in R. A. Thompson: Techniques in Clinical Immunology, 2nd Ed. (1981) 157–169. Blackwell Scientific Publications, Boston, Mass.) Microtiter plates (Immunoplate I, NUNC, Roskilde, Denmark) were coated by incubation overnight with 100 μl per well of a solution of $HbA_{1c}$ (5 μg/ml) or $HbA_o$ (5 μg/ml) in phosphate buffered saline (PBS: $NaH_2PO_4 \cdot H_2O$:0.630 g; $Na_2HPO_4 \cdot 12H_2O$:67,00 g; NaCl 211.9 g; diluted to 25 liters with water) at 4° C. The plates were emptied and blocked with PBS containing 2% w/v of bovine serum albumin (BSA), 200 μl per well at 20° C. for 1 hour, followed by three washes with PBS-Tween-20 (0.05% v/v Tween®-20 in PBS). The undiluted supernatant from a hybridoma culture (50 μl per well) was applied at 20° C. for 1 hour, followed by washing of the plates as described above. The antibody activity against the antogens used for coating was measured colorimetrically by incubating at 20° C. for 1 hour with 100 μl per well of rabbit anti-mouse immunoglobulin conjugated with horse radish peroxidase (Dakopatts A/S, Denmark) diluted 1:1000 in PBS containing 0.5% w/v BSA and, after a further 3 washes, in 0.1 M citrate-phosphate buffer of pH 5.0, and then incubated as described above with o-phenylenediamine (OPD) substrate (o-phenylenediamine, 2HCl:8 mg; citrate-phosphate buffer:15ml; $H_2O_2$ (30 % v/v):5 μl). The reaction was stopped after 3 minutes by the addition of 150 μl of 1 M $H_2SO_4$ and the absorbance at 492 nm was read with a double beam KONTRON SLT-210 photometer (Kontron, Zürich, Switzerland) with the 620 nm reading as reference.

Antibody Dilution Experiments

For these studies, the ELISA was performed as described above, except that increasing volumes, starting from e.g. 0.5 μl, of the supernatants from selected hybridoma cells were diluted with PBS-BSA to a total volume of 100 μ.

Results from the primary screening of ten plates are illustrated in FIG. 1. A substantial number (320) of the supernatants, such as that from hybridoma HEM 13F9, reacted with essentially nonoglycated $HbA_o$, whereas only the antibodies produced by the cells in 2 wells (one antibody designated HEM 13F1 and the other HEM 13F2) reacted preferentially with $HbA_{1c}$.

Figure 2A:
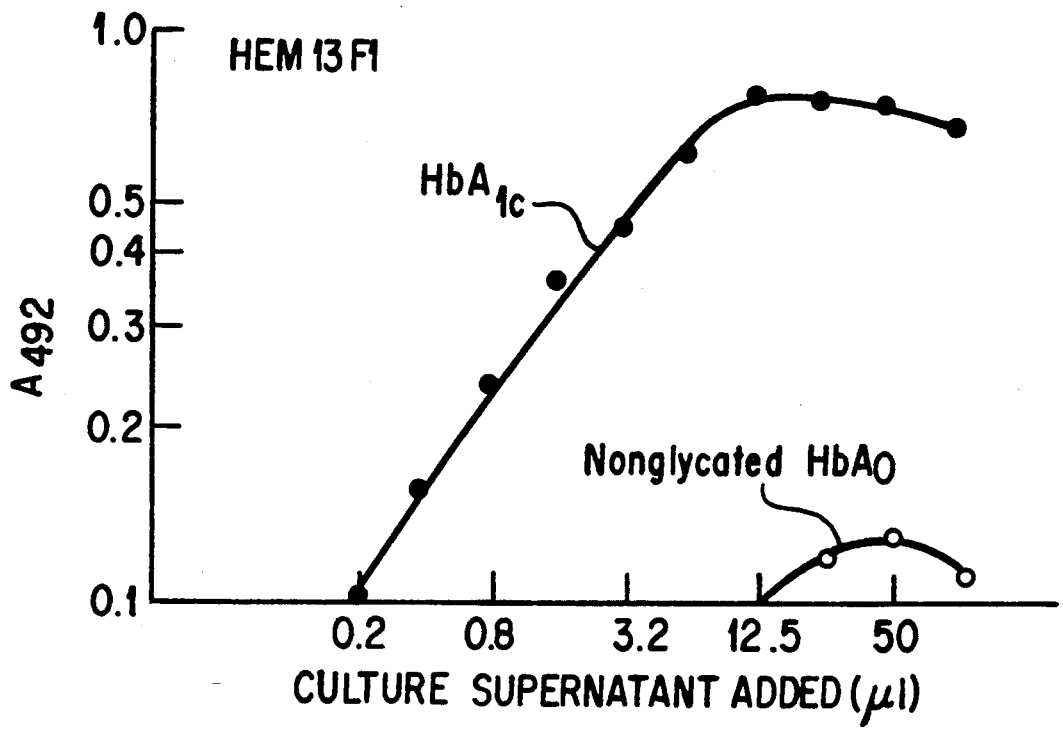
FIG. 2 shows the binding of antibodies obtained from two hybridoma cell lines HEM 13F1 and HEM 13F2 to the immobilized antigens $HbA_{1c}$ and essentially non-glycated $HbA_o$, respectively.
Figure 2B:
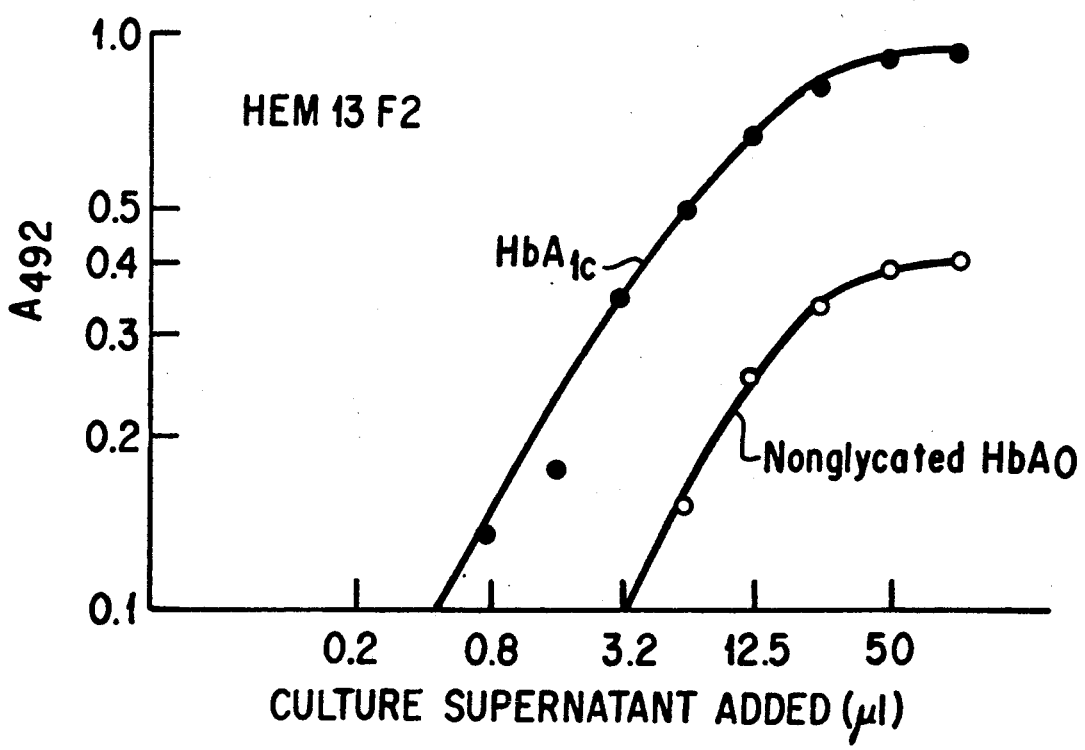

As appears from FIG. 2 of the drawings, dilution experiments with supernatants obtained from hybridoma HEM $13F_1$ and HEM 13F2 for their binding to purified preparations of $HbA_{1c}$ (dots) and $HbA_o$ (circles), respectively, showed that the antibody HEM 13F1 ($IgG_1$) exhibited the greatest specificity for $HbA_{1c}$.

The other antibody, HEM 13F2, also an $IgG_1$ antibody, does not exhibit the same degree of specificity for $HbA_{1c}$ as compared to $HbA_o$, but still shows a preferential binding of $HbA_{1c}$.

Both of the two hybridomas were stabilized in the usual way by recloning under limiting dilution conditions in order to avoid overgrowth of cultures of variant cells no longer producing antibody, thereby facilitating the further production of the respective antibody of each hybridoma. The term "reclone" as used hereinafter refers to a hybridoma cell line derived from a parent hybridoma cell line by cloning under such conditions.

A stable reclone of HEM 13F1 (designated HEM 13F1A4) has been deposited at the European Collection of Animal Cell (ECACC), PHLS Centre for Applied Microbiology and Research Down, Salisbury, Wiltshire SP4 0JG, UK, for the purposes of patent procedure on the date indicated below. ECACC, being an international depository authorized under the Budapest Treaty of 1977, affords permanence of the deposit in accordance with Rule 9 of the Treaty.

| Deposit date: | Depositors Reference: | ECACC Designation: |
|---|---|---|
| 1 February, 1985 | Hybridoma cell line 13F1A4 | 85020101 |

Figure 3:
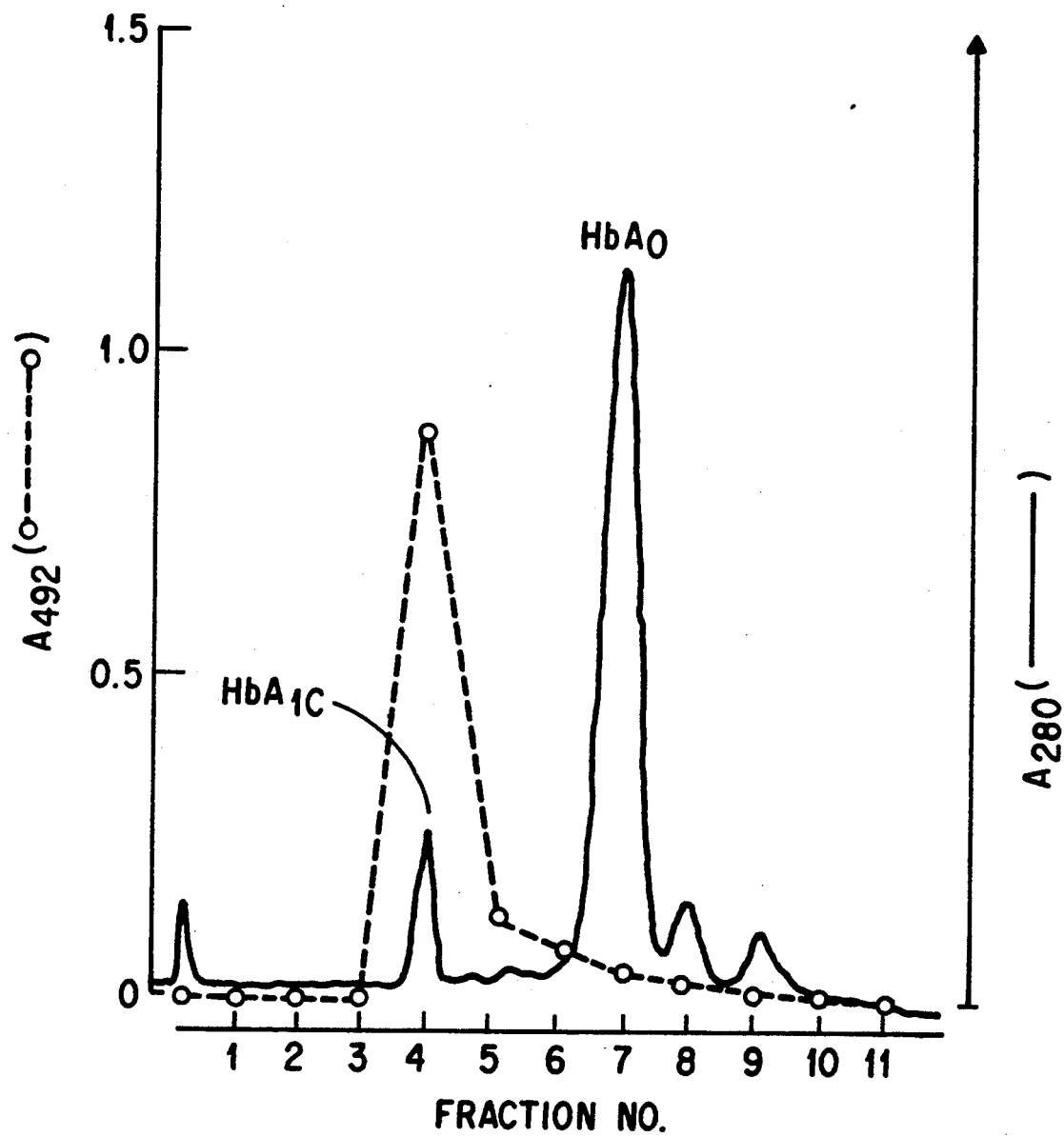
FIG. 3 shows the binding of antibody from HEM 13F1 (broken line) to immobilized fractions of a hemolysate obtained from diabetics. Fractionation of hemoglobin was conducted by cation exchange HPLC (solid line).

The specific binding of the antibody HEM 13F1 to $HbA_{1c}$ is further illustrated in FIG. 3 of the drawings.

Hemoglobin was resolved into its constituents by means of cation exchange HPLC. The collected fractions were tested for their content of antigen (immobilized phase) capable of binding the antibody HEM 13F1 in ELISA. The binding curve so obtained coincided with the $HbA_{1c}$ peak of the HPLC chromatogram whereas essentially no binding capacity was shown for any of the other hemoglobin A constituents.

Figure 4:
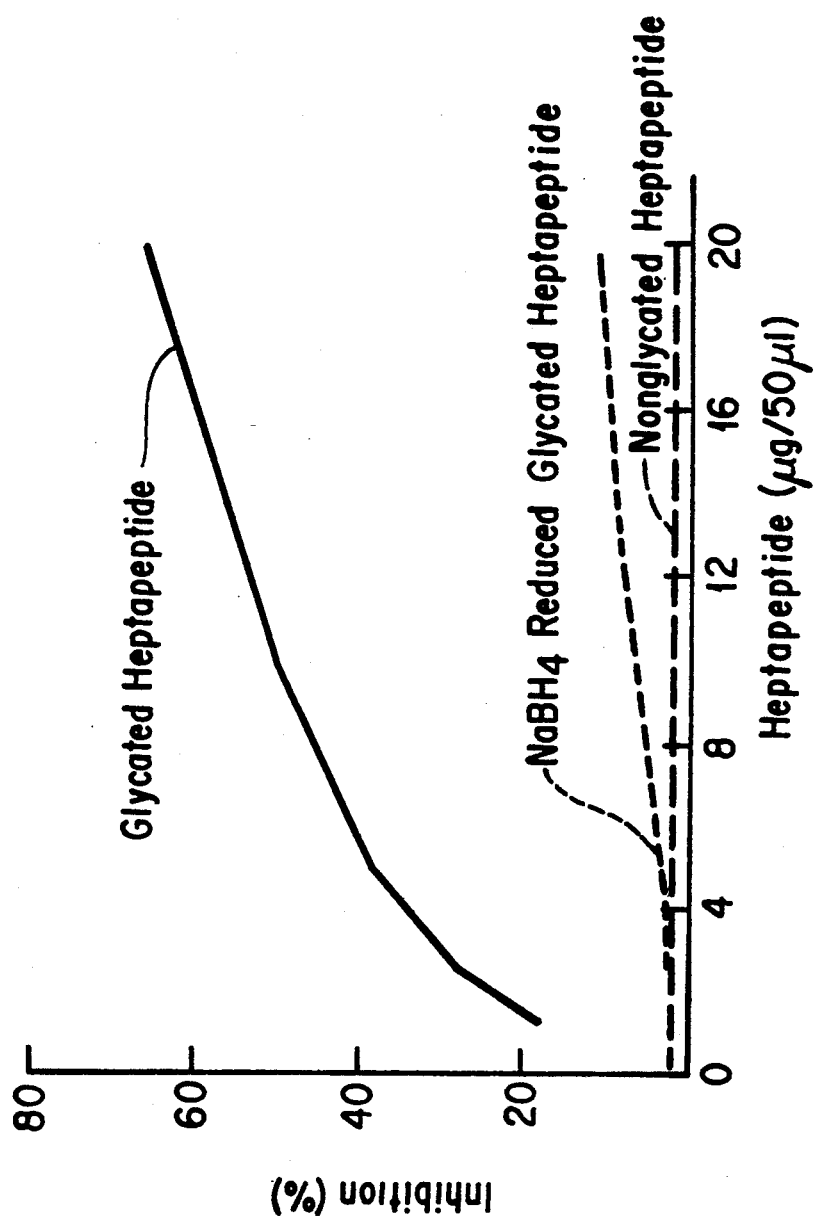
FIG. 4 illustrates studies on inhibition of the binding of antibody HEM 13F1 to $HbA_{1c}$. A synthetic, glycated heptapeptide corresponding to the N-terminal sequence of the β-chain of $HbA_{1c}$, its corresponding reduced derivative and the heptapeptide in non-glycated form were tested.

The inhibition studies illustrated in FIG. 4 of the drawings provide convincing evidence that the epitope recognized by the antibody HEM 13F1 comprises the glycated N-terminal sequence of the $\beta$-chain of $HbA_{1c}$. The data show that whereas the synthetic glycated N-terminal heptapeptide inhibits the binding of antibody HEM 13F1 to immobilized $HbA_{1c}$, only weak or no inhibition is observed for the corresponding reduced derivative and non-glycated heptapeptide, respectively.

Analyses for glycated hemoglobin can be carried out on a hemoglobin source, e.g. hemolysed erythrocytes. The determination can be performed by immunoassay such as by competitive or immunometric assay types. Examples of the latter type are radioimmunometric assays (IRMA) and enzyme-linked immunosorbent assays (ELISA). In a competitive assay the antigen (i.e. the glycated hemoglobin) is labelled with a detectable label. The sample containing the antigen is incubated with the glycated-hemoglobin-specific antibody and the labelled antigen, and after formation of immune complexes, separation and detection, the level of glycated hemoglobin in the sample is determined.

In one preferred mode of performing the immunometric assay the antigen (including that of the sample to be analyzed) is insolubilized on a solid phase, e.g. on the surface of microtiter plate wells. The antibody, e.g. antibody HEM13F1 or an antigen-binding fragment of the antibody is detectably labelled. Incubation of sample with labelled antibody leads to an insolubilized antigen-antibody complex where, after removal of unbound antibody the amount of label is proportional to the amount of antigen.

In another immunometric (sandwich) assay, one antigen-binding antibody is detectably labelled. Another anti-body binding the same antigen is immobilized on a solid phase. Incubation of sample with labelled and immobilized antibody leads to a sandwich, where, after separation of unbound anti-body the amount of label is proportional to the amount of antigen. Immunometric assays can be carried out in forward, reverse or simultaneous modes, depending on the order of addition of the insolubilized and/or labelled antibodies.

Other steps such as washing, stirring, shaking, filtering, or pre-assay extraction of antigen and the like may, of course, be included in the assays, as may be desired or necessary for a particular situation.

The specific concentrations, the temperature and time of incubation, as well as other assay conditions, can be varied depending on such factors as the concentration of the antigen in the sample, the nature of the sample, and the like. Those skilled in the art will be able to determine operative and optimal assay conditions for each determination while employing routine experimentation. For example, the immuno-assay may be run at 4° to 37° C., and each incubation step may be as long as 72 hours.

There are many carriers to which the antigen or antibody can be bound, and which can be used in the present invention. Well-known carriers include glass, polystyrene, polypropylene, polyethylene, dextran, nylon, amyloses, natural and modified celluloses, polyacrylamides, agaroses, and magnetite. The nature of the carrier can be either soluble to some extent or insoluble for purposes of the invention. Those skilled in the art will know many other suitable carriers for binding, or will be able to ascertain such, using routine experimentation.

Depending on the particular embodiment of the assay of the invention, the antibody or an antigen-binding fragment thereof may be coupled with a detectable label such as an enzyme, radioactive isotope, fluorescent compound or metal, chemiluminescent compound, or bioluminescent compound. Furthermore, the binding of these labels to the desired molecule can be done using standard techniques common to those of ordinary skill in the art.

One of the ways in which the antibodies can be detectably labelled is by linking it to an enzyme. This enzyme, in turn, when later exposed to its substrate will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

For increased sensitivity in the ELISA system, the procedures described can be modified using biotinylated anti-body reacting with avidin-peroxidase conjugates.

The amount of antigen can also be determined by labelling the antibody with a radioactive isotope. The presence of the radioactive isotope would then be determined by such means as the use of a gamma counter or a scintillation counter. Isotopes which are particularly useful are $^3H$, $^{125}I$, $^{123}I$, $^{32}P$, $^{35}S$, $^{14}C$, $^{51}Cr$, $^{36}Cl$, $^{57}Co$, $^{58}Co$, $^{59}Fe$, $^{75}Se$, $^{111}$In, $^{99m}Tc$, $^{67}Ga$, and $^{90}Y$.

Determination of the antigen is also possible by labelling the antibody with a fluorescent compound. When the fluorescently labelled molecule is exposed to light of the proper wavelength, its presence can then be detected due to fluorescence of the dye. Among the most important fluorescent labelling compounds are fluorescein isothiocyanate, rhodamine, phycoerythrin, phycocyanin, allophycocyanin, o-phthaldehyde, and fluorescamine.

Fluorescence emitting metal atoms such as Eu (europium), and other lanthanides, can also be used. These can be attached to the desired molecule by means of metal-chelating groups, such as DTPA or EDTA.

Another way in which the antibody can be detectably labelled is by coupling it to a chemiluminescent compound. The presence of the chemiluminescent-tagged immunoglobulin is then determined by detecting the presence of luminescence that arises during the course of a chemical reaction. Examples of particularly useful chemiluminescent labelling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labelling are luciferin, luciferase, and aequorin.

The materials for use in the assay of the invention are ideally suited for the preparation of a kit. Such a kit may comprise a carrier means being compartmentalized to receive in close confinement therein two or more container means such as vials, tubes, and the like, each of said container means comprising one of the separate elements to be used in any desired method.

For example, a first of the said container means useful in immunometric assays may comprise soluble, detectably labelled monoclonal antibody HEM 13F1 in lyophilized form or in solution. In addition the carrier means may also contain at least a second container containing hemoglobin with a predetermined concentration of $HbA_{1c}$ and, preferably, also a third container containing hemoglobin with a predetermined concentration of $HbA_{1c}$ which is different from that of $HbA_{1c}$ in the second container. These latter containers can then be used to prepare a standard curve into which can be interpolated the results obtained from the sample containing the unknown amount of $HbA_{1c}$. Other containers may comprise reagents necessary for determining the amount of labelled antibody and ancillary means, such as buffer solutions.

The invention will now be further illustrated by way of examples which, however, should not be construed as imposing any undue limitations one the scope thereof.

EXAMPLE A

Purification of $HbA_{1c}$

The antigen $HbA_{1c}$ was purified by cation exchange chromatography on a column of Bio-Rex ® 70 (Bio-Rad, Richmond CA, USA) of a hemolysate of washed erythrocytes from diabetics. The method was essentially that described by H. F. Bunn et al. (J.Clin.Invest. 57 (1976) 1652-1659). The source of $HbA_{1c}$ used for primary screening of hybridoma cell cultures, for dilution experiments and in the examples provided hereinafter was a pool of fractions representing the $HbA_{1c}$ peak of the chromatogram.

EXAMPLE B

Preparation of Essentially Non-glycated Hemoglobin $A_o$

Essentially non-glycated hemoglobin $A_o$ was purified by anion exchange chromatography in borate buffer by a modification of the method of R. Shapiro et al., supra as follows:

A 2.5×46 cm column of DEAE Sepharose ® CL-6B (Pharmacia) was equilibrated with eluent I (5 mM/l $K_2B_4O_7$; pH 9.15) at 4° C. A pool of erythrocytes from diabetic subjects was washed three times in isotonic saline, hemolyzed with three volumes of water and freed of membranes by centrifugation. The hemolysate (23 ml) was diluted with 230 ml eluent I and 230 ml water, the pH adjusted to 9.2 with 1 N KOH, and applied to the column at a flow rate of 80 ml/h. The diluted hemolysate was followed by 115 ml eluent I. The hemoglobin was eluted with a gradient from 5 (eluent I; 500 ml) to 50 mM/l $K_2B_4O_7$ (eluent II; pH 9.15; 500 ml) followed by 1000 ml of eluent II.

Three hemoglobin peaks were detected at 540 nm. The second peak, which was the biggest, eluted at about 75% of maximum conductivity and was identified as $HbA_o$. The front part of this peak consisted of essentially non-glycated $HbA_o$, i.e. it contained no glycated lysine residues as determined by the furosine method (E. Schleicher and O. H. Wieland: J.Clin.Chem.Clin.Biochem. 19 (1981) 81-87), and it contained no $HbA_{1c}$. The non-glycated $HbA_o$ was dialysed free of borate and stored at 4° C. in 40 mM/l phosphate buffer with 0.002% chlorhexidine gluconate at pH 7.4.

Essentially non-glycated $HbA_o$ was used as one of the reagents in the primary screening of hybridoma cell culture fluid (FIG. 1) and for the antibody dilution experiments (FIG. 2).

EXAMPLE 1

Immunization and Fusion Experiments

RBF/Dn-strain mice (obtained from the Jackson Laboratory, Bar Harbor, Maine, USA) containing the RB(8.12)5Bnr Robertsonian translocation chromosome were immunized three times at two-week intervals with purified $HbA_{1c}$. $HbA_{1c}$ (20 μg per mouse in PBS, 100 μl) was emulsified 1:1 in Freund's incomplete adjuvant and 200 μl administered subcutaneously (s.c.). The mice were boosted intravenously (i.v.) with 20 μg of $HbA_{1c}$ in 100 μl PBS 20 days following the last s.c. immunization. After another three days the mice were sacrificed and their spleens removed for fusion with myeloma cells.

Spleen cells from two RBF/Dn mice ($8.5 \times 10^7$ cells) were fused with $1.5 \times 10^7$ cells of the FOX-NY myeloma line deficient in the selectable enzyme marker loci adenosine phosphoribosyl transferase ($APRT^-$) and hypoxanthine phosphoribosyl transferase ($HPRT^-$) Thus, the exposure of cell fusion mixtures to a medium requiring APRT-activity ($APRT^+$ selection) eliminates both unfused $APRT^-$ myelomas and $APRT^-$ hybridomas (R. T. Taggart and I. M. Samloff: Science 219 (1983) 1228-1230). The fused cells were seeded on Balb/C-strain mouse macrophage feeder layers in a total of ten 96-well microtiter plates (NUNC, Roskilde, Denmark) in a medium consisting of RPMI-1640 with 15% v/v fetal calf serum (Gibco) supplemented with adenine ($7.5 \times 10^{-5}$ M), hypoxanthine ($8 \times 10^{-4}$ M), aminopterin ($8 \times 10^{-7}$ M) and thymidine ($1.6 \times 10^{-5}$ M), (AHAT).

Cultures were incubated for 12 days at 37° C. in air containing 5% $CO_2$ before being subjected to primary screening

EXAMPLE 2

Isolation of Hybridoma Cells Producing Monoclonal Antibody Specific for $HbA_{1c}$ Hybridomas HEM 13F1 and HEM 13F2 (cf. FIG. 1 of the drawings) were further cloned by limiting dilution in RPMI-1640 medium with 15% (v/v) fetal calf serum a medium containing adenine, aminopterin and thymidine (AAT) as well as in the same medium without these supplements. In both cases the antibodies produced by all the resulting clones showed a preferential binding to $HbA_{1c}$ in the ELISA screening assay. From these cloning experiments recloned stable hybridomas of HEM 13F1 and HEM 13F2 were obtained. The antibodies produced by these recloned hybridomas were identical to and hence showed identical preferential binding specificities to $HbA_{1c}$ compared to those produced by their uncloned parental cell lines HEM 13F1 and HEM 13F2, respectively. Both antibodies were defined as murine $IgG_1$.

A reclone of HEM 13F1, HEM 13F1A4, was selected for the production of antibody for further studies. The antibody produced was characterized by means of a microimmunodiffusion technique against a panel of class and subclass specific antisera. Prior to this test, the antibody in hybridoma supernatants was purified on Protein A-Sepharose ® (Pharmacia, Sweden). In order to ensure binding of the antibody, pH of the supernatants was adjusted to 8.5. Elution was performed with citrate-phosphate buffer, pH 4.5, and the fractions were neutralized with 0.5 M phosphate buffer, pH 7.0, and concentrated by ultrafiltration to approximately 5 mg of protein per ml. Antibody HEM 13F1 was defined as murine $IgG_1$.

EXAMPLE 3

Binding of Antibody HEM 13F1 to $HbA_{1c}$ obtained by Fractionation of a Hemolysate by HPLC A hemolysate prepared as described in Example A was dialysed at 4° C. against a 25 mM/l malonate buffer with pH 6.0 (eluent A). Approximately one mg of hemoglobin in a volume of 30 μl was fractionated on a Mono S ® cation exchange column (0.5×5 cm; Pharmacia) by means of HPLC equipment from Spectra-Physics (Model 8100). Elution was conducted with a gradient made with eluent A and eluent B, the latter consisting of eluent A supplemented with 300 mM/l LiCl. The flow rate was 2 ml per minute and the temperature 37° C. The eluate was monitored at 280 nm and fractions of 2 ml were collected. The chromatogram (solid line) is shown in FIG. 3 of the drawings together with the results (broken line) of ELISA conducted on the collected fractions.

EXAMPLE 4

Antibody Specificity Evaluated by Inhibition Studies

Inhibition analyses were performed with microtiter plates coated with $HbA_{1c}$ and blocked as described under "Primary Screening Procedure". Inhibitors were added in two-fold dilutions (from 20 μg in 50 μl of PBS-BSA) followed by addition of a further 50 μl of antibody HEM 13F1 (2 μg/ml). After incubation of the mixture for 1 hour at 20° C. the amount of bound antibody was determined as previously described. Three compounds were used for inhibition studies, viz. a synthetic, glycated heptapeptide corresponding to the N-terminal region of the β-chains of $HbA_{1c}$ as disclosed in U.S. Pat. No. 4,478,744 (FIG. 4 of the drawings, upper curve); the corresponding reduced heptapeptide derivative, wherein the 1-amino-1-deoxyfructose moiety was reduced with $NaBH_4$ (cf. L. K. Curtiss and J. L. Witztum: J.Clin.Invest. 72 (1983) 1427-1438) (intermediate curve), and the corresponding non-glycated heptapeptide (lower curve). The composition of the peptides used for inhibition studies was verified by amino acid analyses.

EXAMPLE 5

Enzyme Linked Immunosorbent Assay (ELISA) for Glycated Human Hemoglobin $A_{1c}$ ($HbA_{1c}$) in Patient Hemolysates Hemolysates from diabetic and non-diabetic individuals were prepared by lysis of 0.5 ml of erythrocytes in 3.5 ml of distilled water. Two μl of each hemolysate was further diluted in 1 ml of PBS. The diluted material (100 μl) was added to individual wells of microtiter plates (Immunoplate I, NUNC, Roskilde, Denmark) and incubated overnight at 4° C. to allow adsorption of hemoglobin to the surface. The plates were emptied, blocked with BSA (2% w/v in PBS) for 1 hour at room temperature and subsequently washed three times with PBS. Wells with sample material were then incubated for 1 hour with antibody HEM 13F1 (purified IgG$_1$, 5 μg/ml in 100 μl PBS), washed three times with PBS, and incubated for 1 hour with 100 μl of anti-mouse immunoglobulin conjugated with horse radish peroxidase (Dakopatts, Denmark, dil. 1:1000 in PBS). After a further 3 hours of incubation they were washed in sodium citrate buffer, pH 5.0, and incubated for 3 minutes with orthophenylenediamine (OPD) substrate solution (o-phenylenediamine, 2HCl: 8 mg; citrate-phosphate buffer: 15 ml; H$_2$O$_2$ (30% v/v): 5 μl). The reaction was stopped by addition of 150 μl of 1 M H$_2$SO$_4$ and the absorbance read at 492 nm.

Parallel samples were taken of the hemolysates and analysed by isoelectric focusing (IEF) (Mortensen, H. B. and Christoffersen, C.: Biochim.Biophys.Acta 707, (1982) 154-163). Samples were run in duplicate and the results given as percentages of total hemoglobin.

The results from the determination of % HbA$_{1c}$ by means of IEF are compared with the absorbance at 492 nm obtained from ELISA (Table 1). The correlation coefficient r is 0.85.

TABLE 1

Comparison of % HbA$_{1c}$ (IEF) With Values Obtained by ELISA With HEM 13F1 (Mean of Duplicate Determinations)

| Sample | % HbA$_{1c}$ (IEF) | $A_{492}$ (ELISA) |
|---|---|---|
| 1 | 9.6 | 0.490 |
| 2 | 7.0 | 0.420 |
| 3 | 10.2 | 0.560 |
| 4 | 13.1 | 0.749 |
| 5 | 8.5 | 0.585 |
| 6 | 8.8 | 0.590 |
| 7 | 5.9 | 0.261 |
| 8 | 8.4 | 0.480 |
| 9 | 11.2 | 0.650 |
| 10 | 8.5 | 0.495 |
| 11 | 9.0 | 0.630 |
| 12 | 8.3 | 0.410 |
| 13 | 9.5 | 0.488 |
| 14 | 7.9 | 0.490 |
| 15 | 7.0 | 0.460 |
| Mean | 8.9 | 0.517 |
| SD | 1.8 | 0.117 |
| r | 0.85 | |

EXAMPLE 6

Antibody HEM 13F1 Specificity: HbA$_{1c}$ versus pre-HbA$_{1c}$

Blood was drawn from 3 non-diabetic fasting subjects with ethylenediamine tetraacetate (EDTA, 1.5 mg per ml blood). the samples of blood were identified as samples 1, 3 and 4. Blood cells were washed by centrifugation three times with 0.9% NaCl solution.

Three 200 μl portions of packed blood cells were taken from each sample. Two of the samples were incubated with 10 ml of 100 mM glucose in PBS at 20° C. and 37° C., respectively, while the third sample served as a control (stored at 4° C.). Samples were incubated for 16 h, after which they were haemolysed by addition of 1.4 ml H$_2$O containing 200 μl of CCl$_4$ followed by centrifigation. The supernatants (diluted 1:5000 in PBS) were analyzed by ELISA using the antibody HEM 13F1 and, in parallel, by isoelectric focusing (IEF) essentially as described in Example 5 above.

The results from ELISA (expressed as $A_{492}$) are compared with the results from the IEF (expressed as % (pre-HbA$_{1c}$ + HbA$_{1c}$).

TABLE 1

Comparison of % HbA$_{1c}$ (IEF) With Values Obtained by ELISA With HEM 13F1 (Mean of Duplicate Determinations)

| Sample | % HbA$_{1c}$ (IEF) | $A_{492}$ (ELISA) |
|---|---|---|
| 1 | 9.6 | 0.490 |
| 2 | 7.0 | 0.420 |
| 3 | 10.2 | 0.560 |
| 4 | 13.1 | 0.749 |
| 5 | 8.5 | 0.585 |
| 6 | 8.8 | 0.590 |
| 7 | 5.9 | 0.261 |
| 8 | 8.4 | 0.480 |
| 9 | 11.2 | 0.650 |
| 10 | 8.5 | 0.495 |
| 11 | 9.0 | 0.630 |
| 12 | 8.3 | 0.410 |
| 13 | 9.5 | 0.488 |
| 14 | 7.9 | 0.490 |
| 15 | 7.0 | 0.460 |
| Mean | 8.9 | 0.517 |
| SD | 1.8 | 0.117 |
| r | | 0.85 |

The increase in % (pre-HbA$_{1c}$+HbA$_{1c}$) is predominantly due to an increase in % pre-HbA$_{1c}$. The $A_{492}$ value in the ELISA was not significantly affected by incubation of blood cells with 200 mM glucose. It may therefore be concluded that the present monoclonal antibody HEM 13F1 binds preferentially to HbA$_{1c}$ and shows little, if any, cross-reaction with pre-HbA$_{1c}$.

EXAMPLE 7

ELISA for HbA$_{1c}$ in Hemolysates Using Biotinylated HEM 13F1 Antibody

The method used for biotinylation of HEM 13F1 was essentially that described by C. Kendall et al. (J.Immunological Methods 56 (1983) 329-339). The starting material was antibody HEM 13F1 (IgG$_1$), purified as described in Example 2 above. Twelve mg of biotin-N-bydroxy-succinimide (Sigma, St. Louis, USA) was dissolved in 3.5 ml of dimethylformamide (Merck, Darmstadt, FRG) to prepare the biotinylation reagent. A solution of HEM 13F1 IgG$_1$ at 1 mg/ml was prepared in 0.1 M NaHCO$_3$ adjusted to pH 8.5. A mixture of immunoglobulin solution (1 ml) and biotinylation reagent (60 μl) was incubated with stirring for 4 hours at room temperature. After incubation the preparation was dialyzed for 4, 20 and 20 hours against three changes (each of one liter) of PBS, pH 7.2, the last change containing 0.1% NaN$_3$. The biotinylated HEM 13F1 immunoglobulin was stored at 4° C.

Hemolysates from diabetic and non-diabetic individuals were prepared by lysis of 0.5 ml of erythrocytes in 3.5 ml of water and further dilution to approximately 1:1000 in 0.1 M citrate-phosphate buffer of pH 4.0. Diluted samples (100 μl of each) were added to individual wells of microtiter plates (Immunoplate I) and incubated, either overnight or on a mechanical shaker for 30 minutes at room temperature to allow adsorption of hemoglobin to the surface. The plates were emptied, blocked with blocking agent (0.01 M PBS; 0.145 M NaCl; 0.5% (w/v) BSA, pH 7.2) for 30 minutes at room temperature and subsequently washed three times with washing buffer (0.01 M PBS; 0.145 M NaCl; 0.05 % Tween® 20). Wells with sample material were then incubated for 1 hour with 100 μl of a solution of biotin labelled antibody HEM 13F1, approximately 1 μg per ml of buffer (0.01 M PBS; 0.01 M NaCl; 0.5% (w/v) BSA, pH 7.2) followed by washing with buffer. The wells were then incubated with 100 μl of a solution of avidin conjugated with horse radish peroxidase (supplied by VECTOR Laboratories, Inc., CA, USA), diluted 1:10.000 in 0.01 M PBS with 0.5M NaCl; 0.5 (w/v) BSA, pH 7.2. The wells were washed three times with washing buffer and then incubated for 5-10 minutes with OPD substrate solution (Dakopatts, Denmark, Code No. 52000). The reaction was stopped by addition of 100 μl of 1 M $H_2SO_4$ and the absorbance read at 492 nm. Parallel samples of the hemolysates were analyzed in duplicate by IEF.

Absorbance values were converted to percentages of $HbA_{1c}$ of total hemoglobin by means of a standard curve obtained by plotting the absorbance at 492 nm of samples containing known percentages of $HbA_{1c}$ as determined by IEF.

The results obtained from the determination of % $HbA_{1c}$ in a total of 48 individuals by immunoassay and IEF, respectively, are compared in the following Table 2. The correlation coefficient of the two analytical methods is 0.92.

TABLE 2

| Sample | % $HbA_{1c}$ (IEF) | % $HbA_{1c}$ (ELISA) | Sample | % $HbA_{1c}$ (IEF) | % $HbA_{1c}$ (ELISA) |
|---|---|---|---|---|---|
| 1 | 9.6 | 11.2 | 25 | 10.4 | 10.7 |
| 2 | 8.9 | 9.6 | 26 | 10.1 | 10.6 |
| 3 | 10.4 | 10.5 | 27 | 12.1 | 13.1 |
| 4 | 9.2 | 9.6 | 28 | 11.0 | 11.0 |
| 5 | 6.3 | 6.8 | 29 | 11.0 | 11.4 |
| 6 | 7.7 | 8.1 | 30 | 11.0 | 11.6 |
| 7 | 8.9 | 9.4 | 31 | 9.7 | 10.3 |
| 8 | 10.5 | 9.8 | 32 | 10.2 | 10.0 |
| 9 | 12.1 | 12.1 | 33 | 9.3 | 10.7 |
| 10 | 11.1 | 13.1 | 34 | 9.1 | 9.4 |
| 11 | 14.3 | 14.9 | 35 | 10.6 | 11.9 |
| 12 | 10.6 | 11.9 | 36 | 10.0 | 10.5 |
| 13 | 11.0 | 11.9 | 37 | 10.7 | 10.5 |
| 14 | 13.6 | 12.9 | 38 | 8.6 | 8.6 |
| 15 | 11.9 | 13.6 | 39 | 10.2 | 10.3 |
| 16 | 11.1 | 10.8 | 40 | 8.4 | 9.2 |
| 17 | 6.6 | 6.9 | 41 | 9.9 | 11.2 |
| 18 | 9.1 | 10.0 | 42 | 11.0 | 11.3 |
| 19 | 7.7 | 7.9 | 43 | 9.8 | 10.9 |
| 20 | 9.4 | 9.9 | 44 | 13.4 | 12.7 |
| 21 | 7.2 | 7.8 | 45 | 9.4 | 9.5 |
| 22 | 11.6 | 11.9 | 46 | 9.1 | 10.4 |
| 23 | 8.5 | 8.5 | 47 | 9.5 | 10.2 |
| 24 | 8.5 | 8.9 | 48 | 12.7 | 11.2 |
| Mean | | | | 10.1 | 10.5 |
| SD | | | | ±1.7 | ±1.7 |
| r | | | | | 0.921 |

We claim:

1. A method for the determination of glycated hemoglobin ($HbA_{1c}$) in a sample comprising a mixture of $HbA_{1c}$ and non-glycated hemoglobin ($HbA_o$) in the absence of prior denaturation, which comprises:

(A) insolubilizing hemoglobin in said sample on a solid phase;
   (B) contacting said insolubilized hemoglobin with a murine monoclonal antibody which has binding selectivity for $HbA_{1c}$ relative to $HbA_o$ when said $HbA_{1c}$ is insolubilized on a solid phase;
   (C) measuring the amount of bound monoclonal antibody; and
   (D) relating said measured amount of bound monoclonal antibody to the amount of glycated hemoglobin in said sample.

2. A method for the determination of glycated hemoglobin ($HbA_{1c}$) in a sample comprising a mixture of $HbA_{1c}$ and non-glycated hemoglobin ($HbA_o$), consisting essentially of:

(A) insolubilizing hemoglobin in said sample on a solid phase;
   (B) contacting said insolubilized hemoglobin with a murine monoclonal antibody which has binding selectivity for $HbA_{1c}$ relative to $HbA_o$ when said $HbA_{1c}$ is insolubilized on a solid phase;
   (C) measuring the amount of bound monoclonal antibody; and
   (C) relating said measured amount of bound monoclonal antibody to the amount of glycated hemoglobin in said sample.

3. The method of claim 1 or 2 wherein said antibody is produced by the hybridoma cell line having the ECACC designation 85020101.

4. The method of claim 1 or 2 wherein said hemoglobin is insolubilized on a multiwell plate.

5. The method of claim 1 or 2 wherein said monoclonal antibody is detectably labeled.

6. The method of claim 5, wherein said detectable label is an enzyme or a radiolabel.

7. The method of claim 1 or 2 wherein said bound monoclonal antibody is measured by adding thereto a labeled second antibody with specificity therefor.

8. The method of claim 1 or 2 wherein said monoclonal antibody is attached to biotin.

9. The method of claim 8, wherein said attached monoclonal antibody is detected by adding thereto horseradish peroxidase conjugated to avidin.

10. A kit for the determination of glycated human hemoglobin ($HbA_{1c}$), which kit comprises:

(A) a carrier being compartmentalized to receive in close confinement therein two or more containers;
   (B) a first container containing a monoclonal antibody produced by the hybridoma cell line having the designation ECACC 85020101 and having binding selectivity of $HbA_{1c}$ relative to non-glycated hemoglobin ($HbA_o$), when said HbA1c is insolubilized on a solid phase; and
   (C) at least a second container containing $HbA_{1c}$ at a predetermined concentration.

11. The kit of claim 10, wherein said monoclonal antibody is detectably labeled.

12. The kit of claim 11, wherein said detectable label is an enzyme or a radiolabel.

13. The kit of claim 10, which contains a third container containing $HbA_{1c}$ at a predetermined concentration which is different from that of $HbA_{1c}$ in said second container.

* * * * *